(12) United States Patent
Nabulsi et al.

(10) Patent No.: US 8,523,933 B2
(45) Date of Patent: Sep. 3, 2013

(54) ROTATION OPERATED DELIVERY DEVICE

(75) Inventors: Samih Nabulsi, Brisbane (AU); Swee Choong Ng, Sheung Wan (HK); Ben Cramp, Oxley (AU); Neil Davidson, Yeronga (AU); Craig Mounsey, Brisbane (AU); Cambell Smyth, Highgate Hill (AU); Chris Townsend, Gordon Park (AU)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/467,335

(22) Filed: May 9, 2012

(65) Prior Publication Data
US 2013/0131774 A1 May 23, 2013

(30) Foreign Application Priority Data

May 11, 2011 (AU) .................... 2011202175

(51) Int. Cl.
*A61F 2/06* (2013.01)
(52) U.S. Cl.
USPC .......................................... 623/1.11
(58) Field of Classification Search
USPC ............... 623/1.11, 1.12; 606/108, 191, 192, 606/194, 200
See application file for complete search history.

(56) References Cited

U.S. PATENT DOCUMENTS

| | | | |
|---|---|---|---|
| 5,776,142 A | 7/1998 | Gunderson | |
| 6,203,550 B1 | 3/2001 | Olson | |
| 6,669,716 B1 | 12/2003 | Gilson et al. | |
| 6,866,669 B2 | 3/2005 | Buzzard et al. | |
| 7,780,717 B2 * | 8/2010 | Ducke et al. | 623/1.11 |
| 7,789,717 B2 | 9/2010 | Hsiao et al. | |
| 2002/0191516 A1 | 12/2002 | Ito et al. | |
| 2003/0191516 A1 | 10/2003 | Weldon et al. | |
| 2006/0282150 A1 | 12/2006 | Olson et al. | |
| 2007/0255390 A1 | 11/2007 | Ducke et al. | |
| 2011/0270371 A1 * | 11/2011 | Argentine | 623/1.11 |
| 2012/0221091 A1 * | 8/2012 | Hartly et al. | 623/1.11 |

FOREIGN PATENT DOCUMENTS

| | | |
|---|---|---|
| EP | 1369098 A1 | 12/2003 |
| GB | 2474252 A | 4/2011 |
| WO | 9853761 A1 | 12/1998 |
| WO | 03101518 A1 | 12/2003 |
| WO | 2005067819 A1 | 7/2005 |
| WO | 2009/023221 | 2/2009 |

* cited by examiner

*Primary Examiner* — Gary Jackson
*Assistant Examiner* — Lindsey Bachman
(74) *Attorney, Agent, or Firm* — Richard J. Godlewski

(57) ABSTRACT

An endovascular introducer which has a handle assembly, a stent graft deployment device and a stent graft retained on the stent graft deployment device. The handle assembly has a first part and a second part, the second part to be moved relative to the first part. The first part has a fixed portion to be gripped and held by a user and a rotating portion to be rotated. A one way clutch arrangement transfer rotation to co-acting first screw threads so that relative longitudinal motion between the first part and the second part occurs. The deployment device has a pusher assembly and a sheath to cover the stent graft on the pusher assembly. The sheath is connected to the second part so that rotation of the rotating portion causes retraction of the sheath.

12 Claims, 6 Drawing Sheets

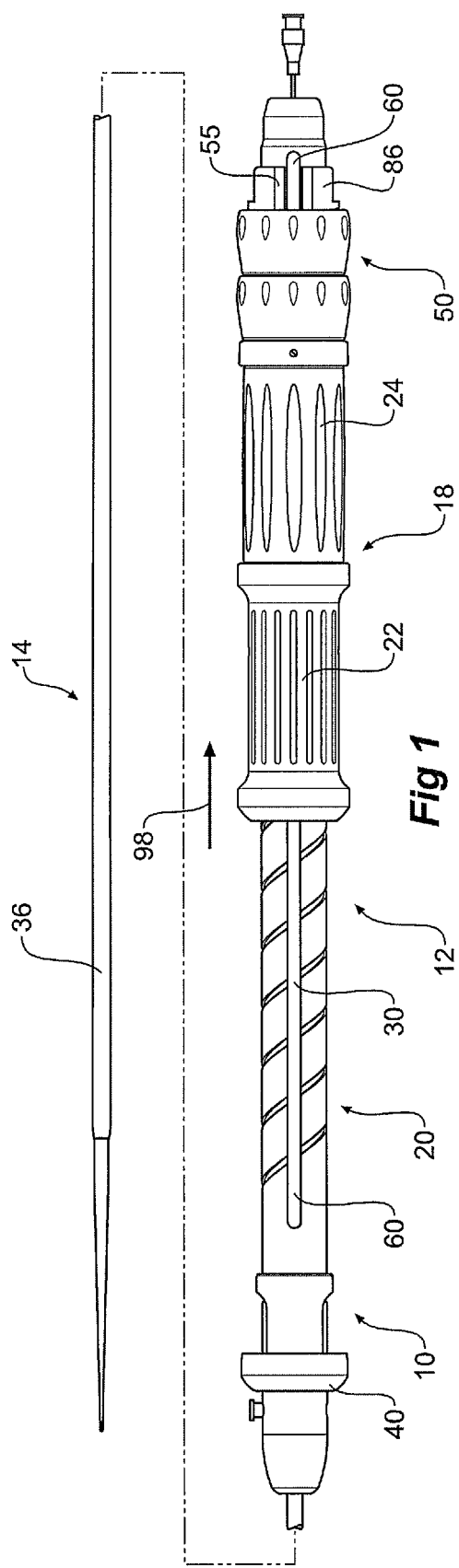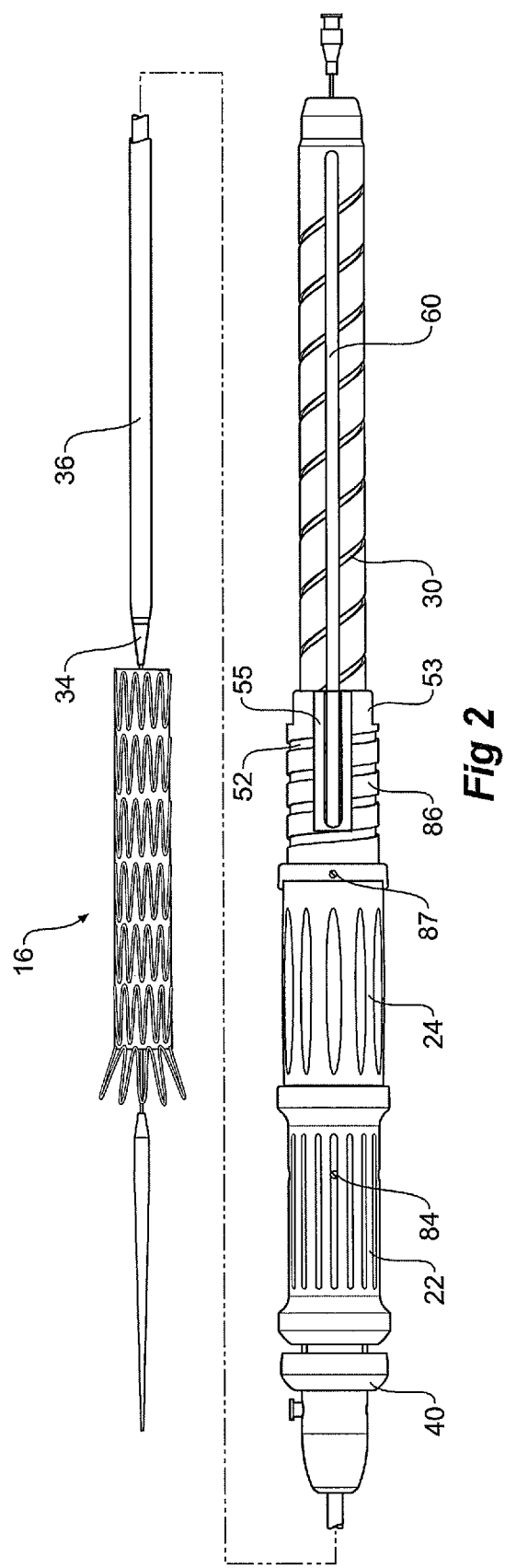

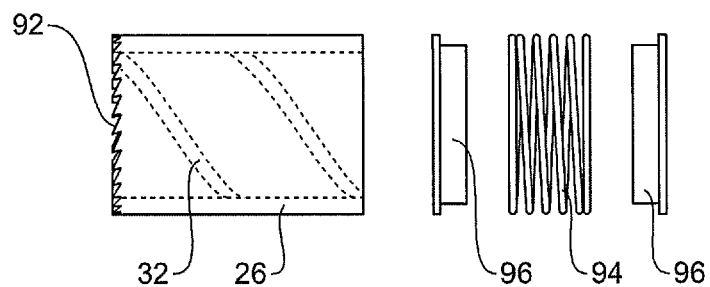
*Fig 5A*
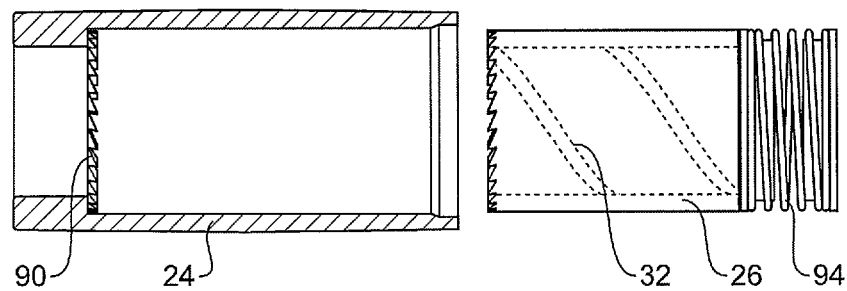
*Fig 5B*
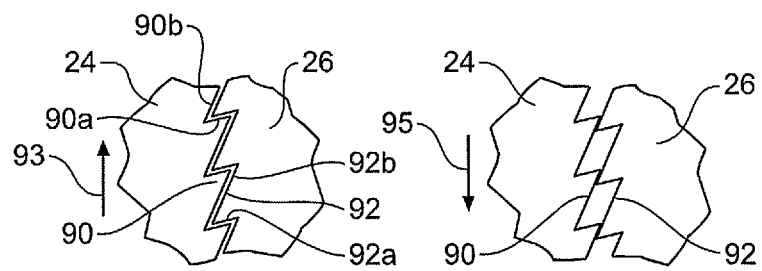
*Fig 5C*          *Fig 5D*

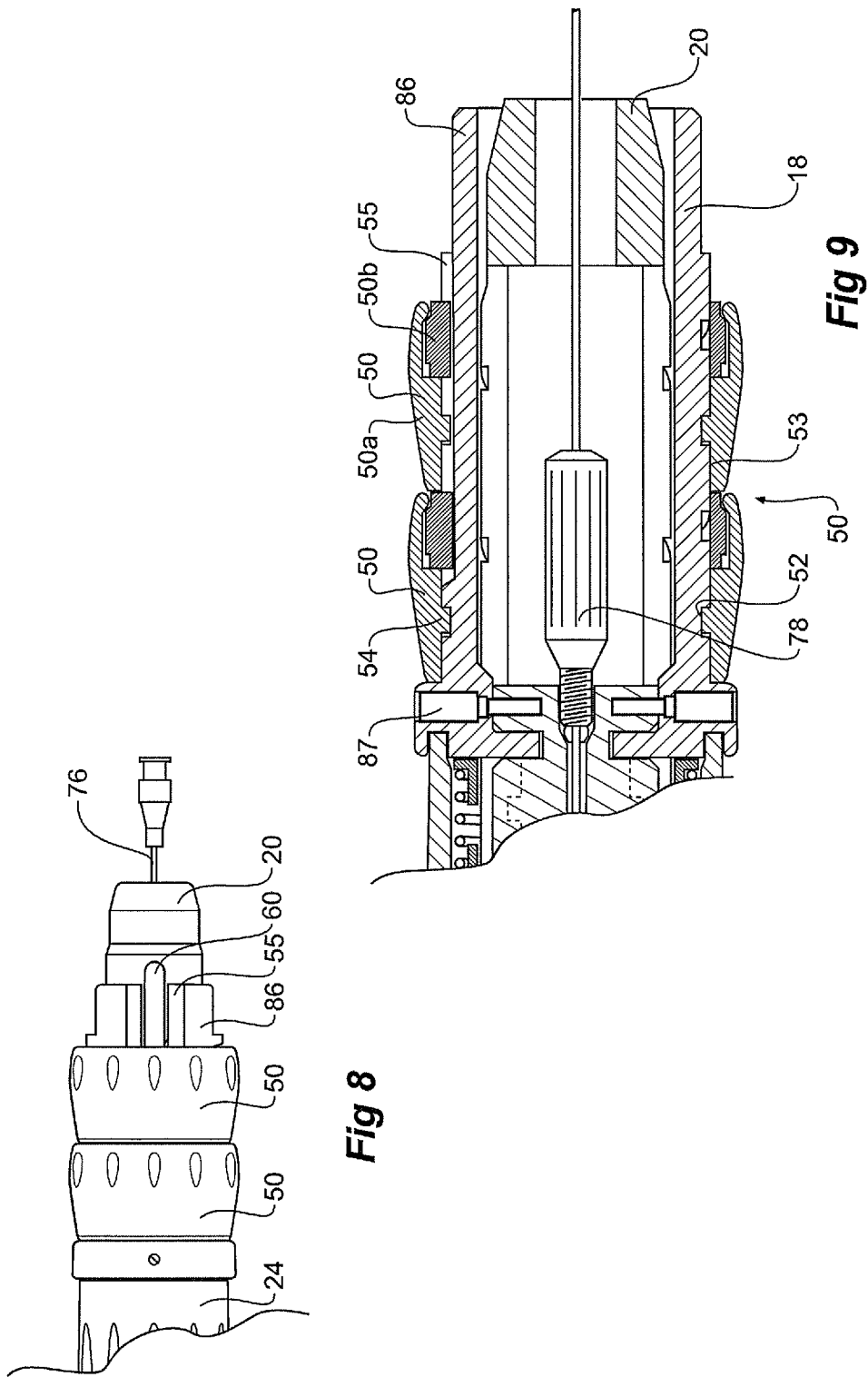

ROTATION OPERATED DELIVERY DEVICE

INCORPORATION BY REFERENCE

The following patent and co-pending patent applications are referred to in the following description:

U.S. Pat. No. 7,780,717 dated Aug. 24, 2010 and entitled "Rotary Handle for Controlled Sequential Deployment".

PCT Patent Publication No. WO 98/53761 entitled "A prosthesis and a method deploying a prosthesis"

PCT Patent Publication WO 03/101518 entitled "Trigger Wire System for a Prosthesis Deployment Device"

The entire content of each of these applications is hereby incorporated by reference.

FIELD OF INVENTION

This invention relates to a deployment device for endovascular stent grafts and more particularly to an arrangement for actuation of such a device.

BACKGROUND OF THE INVENTION

In our earlier patent application, PCT Patent Publication No. WO 98/53761 entitled "A prosthesis and a method deploying a prosthesis" there is disclosed an introducer for a stent graft which retains the stent graft so that each end can be moved independently during the process of endovascular deployment of the stent graft. This device requires that a number of actions be taken in a particular consecutive order to place a stent graft in the required position in the vasculature and then release one end of the stent graft and then another end and if required, between the release of each of the ends, the placement of a branch stent graft from a side arm of the stent graft. These features and other features disclosed in PCT Patent Publication No. WO 98/53761 are incorporated herewith in their entirety into this specification.

It is desirable that the set of sequential actions necessary to release the stent graft at the desired position in the vasculature be undertaken in the required order and that there be less chance for operator error during such a deployment.

It has been found, however, that a stent graft which includes self expanding stents engaging against the inner surface of the sheath, trigger wires retaining the graft onto the pusher as well as the general friction of interacting components can provide significant load. It is the intention of this invention to provide a system to assist with the withdrawing of a sliding portion into the handle of a delivery device.

It is the object of this invention therefore to provide a deployment device which is arranged to introduce, deploy and release a stent graft by a series of sequential actions.

Throughout this specification the term distal with respect to a portion of the aorta, a deployment device or a prosthesis means the end of the aorta, deployment device or prosthesis further away in the direction of blood flow away from the heart and the term proximal means the portion of the aorta, deployment device or end of the prosthesis nearer to the heart. When applied to other vessels similar terms such as caudal and cranial should be understood.

The invention will in general be discussed in relation to deployment of a stent graft into the abdominal aorta but the invention is not so limited and can apply to deployment into other portions of the aorta or into other vessels of the human or animal body.

Throughout this discussion the term "stent graft" is intended to mean a device which has a tubular body of biocompatible graft material and at least one stent fastened to the tubular body to define a lumen through the stent graft. The stent graft may be bifurcated and have fenestrations, side arms or the like. Other arrangements of stent grafts are also within the scope of the invention.

DESCRIPTION OF THE INVENTION

In one form therefore, the invention is said to reside in an endovascular introducer comprising in combination, a handle assembly, a stent graft deployment device and a stent graft retained on the stent graft deployment device, the handle assembly including a first part and a second part, the second part to be moved relative to the first part, the first part comprising a fixed portion to be gripped and held by a user, a rotating portion to be rotated with the fixed portion and a rotation transfer sleeve, the rotation transfer sleeve being within the rotating portion and connected to the rotating portion by a one way clutch arrangement whereby rotation of the rotating portion in a first direction transfers rotation to the rotation transfer sleeve and rotation of the rotating portion in a direction opposite to the first direction does not transfer rotation to the rotation transfer sleeve; the rotation transfer sleeve and the second part comprising co-acting first screw threads whereby rotation of the rotating portion of the first part with respect to the second part in the first direction transferred through the one way clutch arrangement causes relative longitudinal motion between the first part and the second part; the deployment device including a pusher assembly, the stent graft being mounted onto the pusher assembly and a sheath to cover the stent graft on the pusher assembly and to retain the stent graft in a compressed condition on the pusher assembly, the sheath being relatively movable with respect to the pusher assembly, the pusher assembly being connected to the first part and the sheath being connected to the second part whereby retraction of the second part with respect to the first part by the relative rotation thereof causes the sheath to be retracted at least partially from the stent graft on the pusher assembly.

Preferably the rotation transfer sleeve comprises an internal cylindrical surface and the first screw thread is formed thereon.

Preferably the second part comprises a cylindrical tube surrounding the pusher assembly, the cylindrical tube including at least one longitudinal slot and the fixed portion of the first part being engaged with the pusher assembly through the longitudinal slot whereby the second part can move longitudinally with respect to the pusher assembly and the first part.

Preferably the one way clutch assembly comprises the rotation transfer sleeve comprising a first ring of gear teeth and the rotating portion comprising a second ring of gear teeth, the first ring of gear teeth engaging with the second ring of gear teeth when the rotating portion is rotated in the first direction and the first ring of gear teeth disengaging with the second ring of gear teeth when the rotating portion is rotated in the second direction.

Preferably the one way clutch assembly further comprises a resilient apparatus resiliently engaging the first ring of gear teeth engaging with the second ring of gear teeth.

Preferably the first ring of gear teeth and the second ring of gear teeth each comprise a plurality of teeth, each tooth comprising leading flat face and an angled trailing face when viewed in the first direction whereby when the rotating portion is rotated in the first direction the leading flat face of a tooth of the rotating portion engages with the leading flat face of a tooth of the rotation transfer sleeve to transfer rotation and when the rotating portion is rotated in the second direction the angled trailing face of a tooth of the rotating portion engages with the angled trailing face of a tooth of the rotation transfer sleeve and the angled faces of the respective teeth cause separation of the respective gear rings thereby preventing transfer of rotation.

Preferably the fixed portion comprises first and second trigger wire release mechanisms at a distal end thereof, the first and second trigger wire release mechanisms being connected to trigger wires which engage the sent graft to temporarily retain the stent graft to the stent graft deployment device, the first and second trigger wire release mechanisms being movable to be disengaged from the distal end of the fixed portion to pull the trigger wires to release the stent graft from the stent graft deployment device.

Preferably the first and second trigger wire release mechanisms are engaged onto the distal end of the fixed portion by respective interengaging screw threads and the first and second trigger wire release mechanisms are movable to be disengaged from the distal end of the fixed portion by being rotated with respect to the fixed portion.

Preferably each of the first and second trigger wire release mechanisms comprise a rotating portion and a linearly moving portion, the linearly moving portion being engaged into a longitudinal track in the fixed portion and the interengaging screw thread being on the rotating portion and the trigger wires being affixed to the linearly moving portion.

Preferably the sheath comprises a sheath hub and the sheath hub is releasably engaged with a proximal end of the second part.

Preferably the releasable engagement of the sheath hub with the proximal end of the second part comprises a hub shroud around the hub and a locking ring, the locking ring engaging the hub shroud and incorporating a bayonet interconnection with the proximal end of the second part, whereby rotation of the locking ring disengages the bayonet interconnection with the proximal end of the second part such that the hub shroud and locking ring can be removed from the proximal end of the second part.

In an alternative form the invention comprises an endovascular introducer comprising in combination, a handle assembly, a stent graft deployment device and a stent graft retained on the stent graft deployment device, the handle assembly including a first part and a second part, the second part to be moved relative to the first part, the first part comprising a fixed portion to be gripped and held by a user, a rotating portion to be rotated with the fixed portion and a rotation transfer sleeve, the rotation transfer sleeve being within the rotating portion and connected to the rotating portion by a one way clutch arrangement whereby rotation of the rotating portion in a first direction transfers rotation to the rotation transfer sleeve and rotation of the rotating portion in a direction opposite to the first direction does not transfer rotation to the rotation transfer sleeve; the rotation transfer sleeve and the second part comprising co-acting first screw threads whereby rotation of the rotating portion of the first part with respect to the second part in the first direction transferred through the one way clutch arrangement causes relative longitudinal motion between the first part and the second part, the one way clutch assembly comprises the rotation transfer sleeve comprising a first ring of gear teeth and the rotating portion comprising a second ring of gear teeth, the first ring of gear teeth engaging with the second ring of gear teeth when the rotating portion is rotated in the first direction and the first ring of gear teeth disengaging with the second ring of gear teeth when the rotating portion is rotated in the second direction and a spring to engage the first ring of gear teeth with the second ring of gear teeth; the deployment device including a pusher assembly, the stent graft being mounted onto the pusher assembly and a sheath to cover the stent graft on the pusher assembly and to retain the stent graft in a compressed condition on the pusher assembly, the sheath being relatively movable with respect to the pusher assembly, the pusher assembly being connected to the first part and the sheath being connected to the second part whereby retraction of the second part with respect to the first part by the relative rotation thereof causes the sheath to be retracted at least partially from the stent graft on the pusher assembly.

It will be seen that by this invention there is disclosed a stent graft delivery device where retraction of the sheath from the stent graft mounted onto the delivery device is achieved by rotation of the rotating portion in the first direction which transfers the rotation to the rotation transfer sleeve via the one way clutch arrangement. In turn the rotation transfer sleeve transfers the rotation to longitudinal movement of the second part which retracts the sleeve from the stent graft on the delivery device.

If the rotating portion is rotated in the second direction the one way clutch arrangement is disengaged and the rotation transfer sleeve does not rotate and hence longitudinal movement of the second part does not occur. The disengagement occurs because the respective angled faces of the opposed gears slide over each other rather than transfer rotation.

If rotation could be transferred in the second direction that would cause the second part to advance on the stent graft and this would cause significant problems to the stent graft.

A physician using the device can in effect use the delivery device of the present invention in two different ways. In a first method the physician can hold the fixed portion of the first part in one hand and grip the rotating portion in the other hand. Then by a reciprocating wrist motion with engagement in a first direction and disengagement in a second direction the sheath can be withdrawn. At any stage retraction of the sheath can be stopped to enable the physician to monitor the progress of the release of the stent graft and reposition it if necessary. In a second method the physician can hold the fixed portion of the first part in one hand and grip the rotating portion in the other hand while rotating in the first direction and then release it while the hand is moved backwards to re-grip the rotating portion and then rotate it again in the first direction.

At any desired stage during the retraction of the sheath from the stent graft the physician can activate the first and second trigger wire release mechanisms at a distal end of the first portion. The first and second trigger wire release mechanisms are normally mounted onto the distal end of the first portion so that the more distal one can be moved first and this is attached the trigger wire or wires which engage the proximal end of the stent graft to temporarily retain the proximal end of stent graft to the stent graft deployment device. This would normally be done after the sheath is about half withdrawn and the physician is happy about the positioning of the proximal end. Subsequently after the sheath has been fully retracted to fully expose the stent graft and the distal end of the stent graft has been correctly positioned the second trigger wire release mechanism can be activated and this is attached the trigger wire or wires which engage the distal end of the stent graft to temporarily retain the distal end of stent graft to the stent graft deployment device.

BRIEF DESCRIPTION OF THE DRAWINGS

This then generally describes the invention but to assist with understanding reference will now be made to the accompanying drawings which show a preferred embodiment of the invention.

In the drawings:

FIG. 1 shows a side view of a delivery device according to one embodiment of the present invention;

FIG. 2 shows the embodiment of FIG. 1 with the sheath fully retracted;

FIG. 5A shows detail of the rotation transfer sleeve and spring;

FIG. 5B shows detail of the rotation portion in cross section and the rotation transfer sleeve and spring;

FIG. 5C shows detail of the teeth on the rotation transfer sleeve and rotation portion when they are engaged;

FIG. 5D shows detail of the teeth on the rotation transfer sleeve and rotation portion when they are disengaged;

FIG. 8 shows a detailed view of the trigger wire release section; and

FIG. 9 shows detailed cross sectional view of the trigger wire release section.

DESCRIPTION OF PREFERRED EMBODIMENTS

Figure 3:
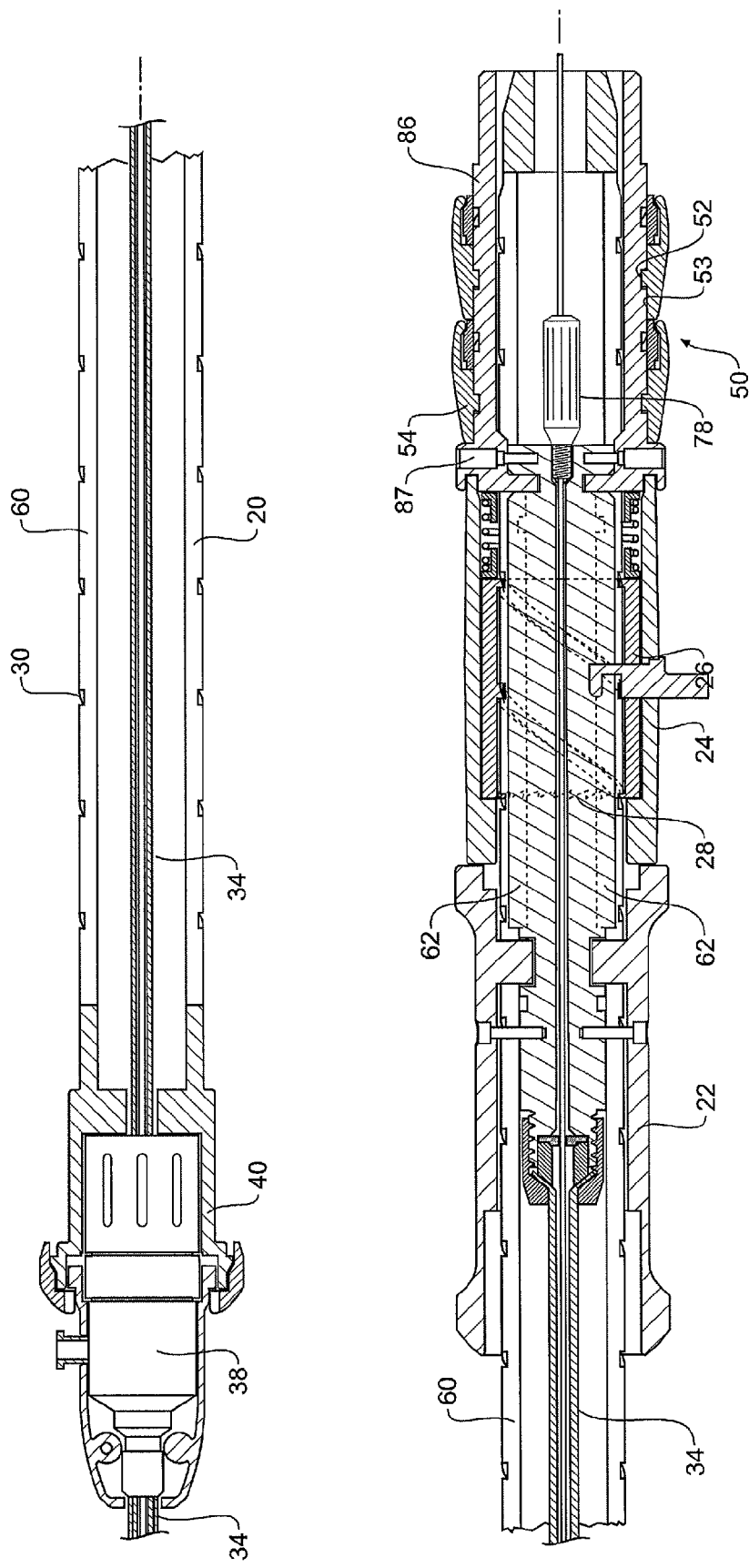
FIG. 3 shows a cross section view of part of the embodiment of FIG. 1.

FIGS. 1 to 3 show a first embodiment of an endovascular introducer comprising in combination, a handle assembly, a stent graft deployment device and a stent graft retained on the stent graft deployment device. FIG. 1 shows a side view of a delivery device according to one embodiment of the present invention in a ready to deploy configuration, FIG. 2 shows the embodiment of FIG. 1 with the sheath fully retracted and FIG. 3 shows a cross section view of part of the embodiment of FIG. 1.

Figure 4:
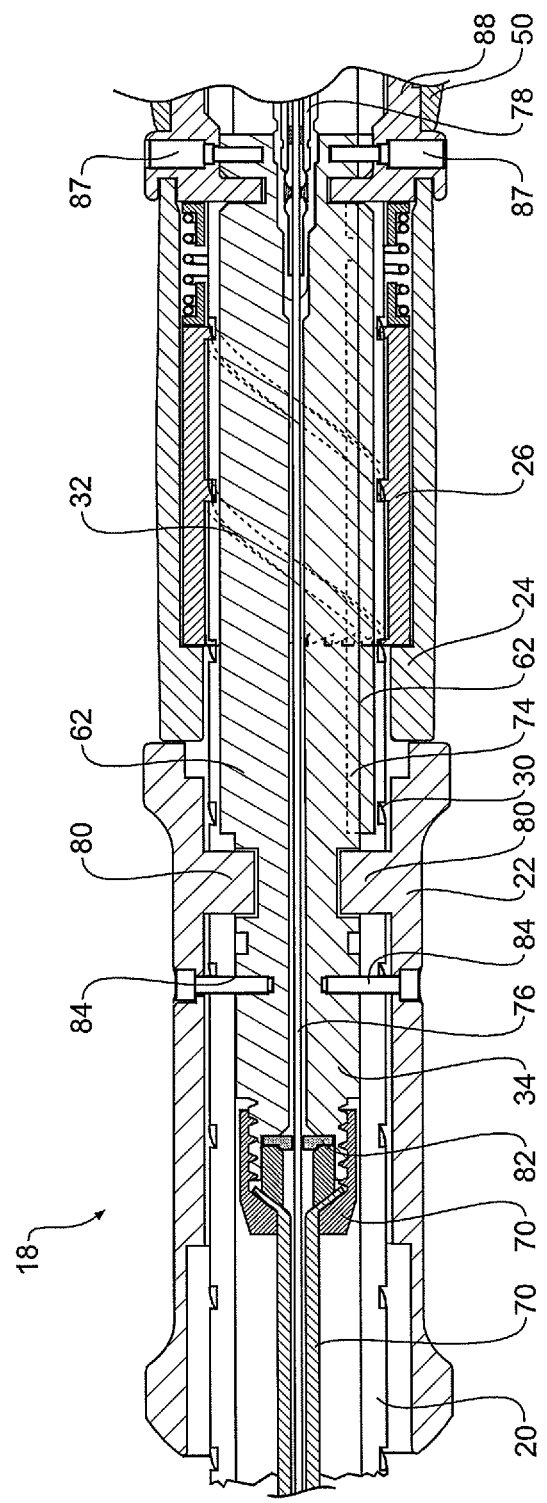
FIG. 4 shows a detail of part of the handle portion shown in FIG. 3.

The endovascular introducer 10 comprises a handle assembly 12, a stent graft deployment device 14 and a stent graft 16 retained on the stent graft deployment device. The handle assembly 12 includes a first part 18 and a second part 20, the second part to be moved relative to the first part. The first part comprises a fixed portion 22 to be gripped and held by a user, a rotating portion 24 to be rotated with the fixed portion and a rotation transfer sleeve 26 (see FIG. 3) The rotation transfer sleeve is within the rotating portion and connected to the rotating portion by a one way clutch arrangement 28 whereby rotation of the rotating portion in a first direction transfers rotation to the rotation transfer sleeve and rotation of the rotating portion in a direction opposite to the first direction does not transfer rotation to the rotation transfer sleeve. More detail of the handle portion is shown in FIG. 4 and discussed below.

The rotation transfer sleeve 26 and the second part 20 comprising co-acting first screw threads. Thread 30 on the second part and thread 32 on the inner surface of the rotation transfer sleeve 26. By this arrangement rotation of the rotating portion 24 of the first part 18 with respect to the second part 20 in a first direction transfers rotation through the one way clutch arrangement and thereby causes relative longitudinal motion between the first part 18 and the second part 20. More detail of the construction and operation of the one way clutch assembly is shown in FIGS. 5A to 5D and discussed below.

Figure 6:
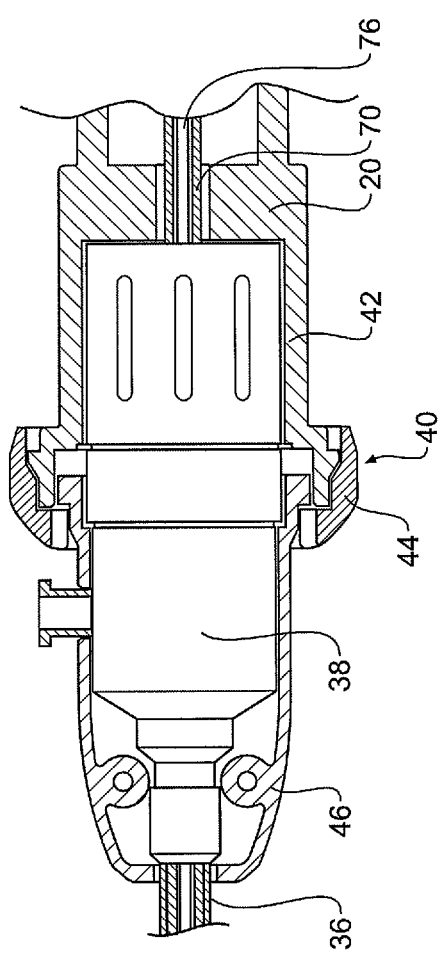
FIG. 6 shows detail of the housing for the hub on the sleeve.

The deployment device includes a pusher assembly 34, the stent graft being mounted onto the pusher assembly and a sheath 36 to cover the stent graft 16 on the pusher assembly and to retain the stent graft in a compressed condition on the pusher assembly. The sheath is relatively movable with respect to the pusher assembly. The pusher assembly 34 is connected to the first part 18 and the sheath 36 is connected to the second part 20 so that retraction of the second part 20 with respect to the first part 18 by the relative rotation thereof causes the sheath to be retracted at least partially from the stent graft on the pusher assembly. The sheath has a hub assembly 38 at its distal end and the hub assembly is received in a releasable housing 40 at the proximal end of the second part 20. More detail of the releasable housing is shown in FIG. 6 and discussed below.

The second part 20 has the thread 30 on its outer surface along substantially its entire length as can be seen in FIGS. 1 and 2. The second part 20 also has a longitudinal slot 60 on both its upper and lower surfaces. The purpose of the longitudinal slot 60 is to allow a connection between the various components of the first part with the pusher assembly 34 as well as to prevent relative rotation of the pusher assembly and the second part. For this purpose the pusher assembly 34 has a pair of radially extending flanges 62 which are received in the longitudinally extending slot 60. These flanges 62 allow relative longitudinal movement between the pusher assembly and the second part but not relative rotational movement.

At the distal end of the first part 18 is a trigger wire release mechanisms 50 as will be discussed in more detail with respect to FIGS. 7 and 8.

FIG. 4 shows a detail of part of the handle portion shown of the device shown in FIGS. 1 to 3. The pusher assembly comprises a pusher catheter 70 extending proximally from a fastening nut 72 at the proximal end of a pusher body 74. A guide wire cannula 76 extends through the pusher body and pusher catheter and can be locked for preventing relative movement of the guide wire cannula 76 with respect to the pusher body by a pin vice assembly 78 at the distal end of the pusher body. A haemostatic sealing flange 82 seals around the guide wire cannula 76 and is held in place by the nut 70. The pusher body 74 has the flanges 62 on it which extend into the longitudinal slot 60 to allow relative longitudinal movement between the pusher body and the second part but not relative rotational movement.

The fixed portion 22 of the first part 18 has inwardly extending lugs 80 which also extend through the longitudinal slot 60 and into the pusher body 74 to prevent rotation of the fixed part with respect to the pusher body 74. Screws 84 also fasten the fixed portion 22 of the first part 18 to the pusher body 74.

The distal end 86 of the first part which is distal of the rotating portion 24 is also fastened to the pusher body 74 by screws 87. The distal end of the first part supports the trigger wire release mechanisms 50 as will be discussed in more detail with respect to FIGS. 7 and 8.

The construction and operation of the one way clutch assembly is shown in FIGS. 5A to 5D. FIG. 5A shows detail of the rotation transfer sleeve and spring, FIG. 5B shows detail of the rotation portion in cross section and the rotation transfer sleeve and spring, FIG. 5C shows detail of the teeth on the rotation transfer sleeve and rotation portion when they are engaged and FIG. 5D shows detail of the teeth on the rotation transfer sleeve and rotation portion when they are disengaged.

Retraction of the sheath 36 from the stent graft 16 to release the stent graft once the stent graft has been correctly positioned in the vasculature of a patient is achieved by rotation of the rotating portion 24 by a physician while the physician grasps the fixed portion 22 of the first part 18.

The rotating portion has teeth 90 on its inner surface and the rotation transfer sleeve has teeth 92 on its end. The teeth 90 and 92 are sawtooth teeth each comprising an angled face 90a, 92a and a vertical face 90b and 92b, the two sets of teeth having opposite configurations so that the vertical faces engage each other and the angled faces engage each other.

Rotation of the rotating portion 24 causes the teeth 90 in its inner surface to engage with the teeth 92 on the end of the rotation transfer sleeve 26 and transfer rotation when the rotating portion 24 is rotated in a first direction as schematically indicated in FIG. 5C by the arrow 93. The spring 94 carried on spring supports 96 causes the teeth 92 to remain engaged with the teeth 90. When, however, the rotating portion 24 is rotated in a second direction opposite to the first direction as schematically indicated in FIG. 5D by the arrow 95 the teeth 90 the angled faces cause the opposed teeth to spread apart against the loading of the spring 94 and the teeth ratchet over each other without transferring rotation.

The rotational transfer sleeve 26 has the screw thread 32 on its inner surface and this engages with the screw thread 30 on the outer surface of the second part 20 and rotation of the rotation transfer sleeve is converted to longitudinal movement of the second part in a distal direction as shown by the arrow 98 in FIG. 1. This movement in turn causes the sheath to be retracted from the stent graft as discussed above. It is undesirable for the sheath to be moved proximally on the stent graft and hence the one way clutch assembly prevents this proximal movement.

A physician using the delivery device 10 can in effect use it in two different ways. In a first method the physician can hold the fixed portion 22 of the first part 18 in one hand and grip the rotating portion 24 in the other hand. Then by a reciprocating wrist motion with engagement in one direction and disengagement in the other direction the sheath 36 can be withdrawn. At any stage retraction of the sheath can be stopped to enable the physician to monitor the progress of the release of the stent graft and reposition it if necessary. In a second method the physician can hold the fixed portion 22 of the first part 18 in one hand and grip the rotating portion 24 in the other hand while rotating in one direction and then release while the moving his hand backwards to re-grip the rotating portion and then grip and rotate it again in the first direction.

FIG. 6 shows detail of the housing for the sleeve hub and the sleeve on the pusher assembly. The sheath 36 has a hub assembly 38 at its distal end and the hub assembly is received in a releasable housing 40 at the proximal end of the second part 20. The releasable housing 40 comprises a socket 42 into which the hub 38 is received and a bayonet fitted locking nut 44 engages against the releasable housing 40 and holds a forward part 46 of the housing against the housing and capturing the hub 38.

In the case of a problem during deployment of a stent graft in which it is desirable to more manually operate the delivery device the nut 44 can be released to enable removal of the hub. At the same time the various components of the handle can be dismantled.

Figure 7:
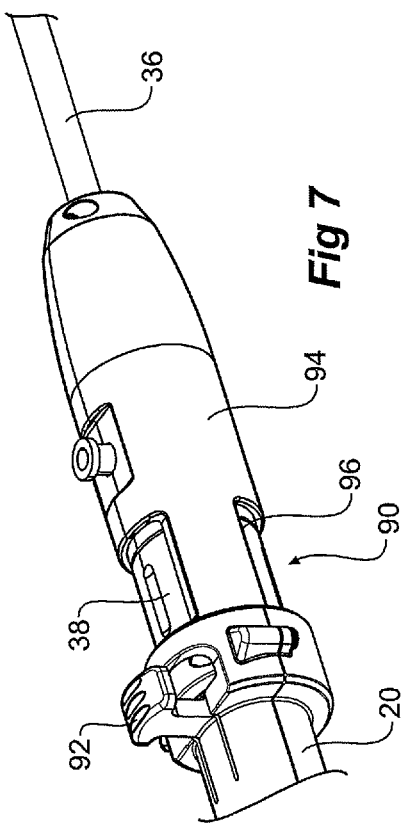
FIG. 7 shows detail of an alternative housing for the hub on the sleeve.

FIG. 7 shows detail of the housing 90 for the sheath hub 38 and sheath 36. The sheath 36 has a hub assembly 38 at its distal end and the hub assembly is received in a releasable housing 90 at the proximal end of the second part 20. The releasable housing 90 comprises a socket 94 into which the hub 38 is received and there is a releasable engagement of the socket to the proximal end of the second part 20 with a bayonet type engagement. Movement of the bayonet type fitting from an engaged to a disengaged position is restricted by a button 92. The releasable housing 90 has openings 96 through which the haemostatic valve of the hub 38 can be operated.

Depression of the button 92 enables the socket 94 to be rotated enough to remove it from the bayonet fitting and be released from the proximal end of the second part 20. The socket stays with the hub 38 while the handle portion can be withdrawn from it, which withdraws, in turn, the pusher, the guide wire cannula and the nose cone dilator.

In the case of a problem during deployment of a stent graft in which it is desirable to more manually operate the delivery device the button 92 can be depressed and the socket released to enable removal of the hub. At the same time the various components of the handle assembly can be dismantled.

FIG. 8 shows a detailed view of the trigger wire release section and FIG. 9 shows detailed cross sectional view of the trigger wire release section. The distal end of the first part 18 supports the trigger wire release mechanisms 50. The distal end of the first part 18 has a screw thread 52 on its outer surface 53. Each of the trigger wire release devices 50 have an internal screw thread 54 which engages into the screw thread 52. Each release device 50 has a rotating part 50a and a longitudinally moving part 50b. The longitudinally moving part 50b has a tongue which engages into a track 55 on the outer surface 53 of the distal end of the first part 18 and this tongue allows transfer of the rotation of the part 50a to longitudinal movement of the part 50b. The part 50a can rotate with respect to the part 50b. Trigger wires for release of the stent graft (not shown) are fastened to the part 50b so that rotation of the part 50a causes longitudinal movement of the part 50b which in turn pulls the respective trigger wire.

PCT Patent Publication No. WO 98/53761 entitled "A prosthesis and a method deploying a prosthesis" and PCT Patent Publication WO 03/101518 entitled "Trigger Wire System for a Prosthesis Deployment Device" teach trigger wire systems and trigger wire release arrangement and the teachings therein a incorporated herein in their entirety.

The claims defining the invention are as follows:

1. An endovascular introducer comprising in combination, a handle assembly, a stent graft deployment device and a stent graft retained on the stent graft deployment device, the handle assembly including a first part and a second part, the second part to be moved relative to the first part, the first part comprising a fixed portion to be gripped and held by a user, a rotating portion to be rotated with the fixed portion and a rotation transfer sleeve, the rotation transfer sleeve being within the rotating portion and connected to the rotating portion by a one way clutch arrangement whereby rotation of the rotating portion in a first direction transfers rotation to the rotation transfer sleeve and rotation of the rotating portion in a direction opposite to the first direction does not transfer rotation to the rotation transfer sleeve;

the rotation transfer sleeve and the second part comprising co-acting first screw threads whereby rotation of the rotating portion of the first part with respect to the second part in the first direction transferred through the one way clutch arrangement causes relative longitudinal motion between the first part and the second part, the deployment device including a pusher assembly, the stent graft being mounted onto the pusher assembly and a sheath to cover the stent graft on the pusher assembly and to retain the stent graft in a compressed condition on the pusher assembly, the sheath being relatively movable with respect to the pusher assembly, the pusher assembly being connected to the first part and the sheath being connected to the second part whereby retraction of the second part with respect to the first part by the relative rotation thereof causes the sheath to be retracted at least partially from the stent graft on the pusher assembly.

2. An endovascular introducer as in claim 1 wherein the rotation transfer sleeve comprises an internal cylindrical surface and the first screw thread is formed thereon.

3. An endovascular introducer as in claim 1 wherein the second part comprises a cylindrical tube surrounding the pusher assembly, the cylindrical tube including at least one longitudinal slot and the fixed portion of the first part being engaged with the pusher assembly through the longitudinal slot whereby the second part can move longitudinally with respect to the pusher assembly and the first part.

4. An endovascular introducer as in claim 1 wherein the one way clutch assembly comprises the rotation transfer sleeve comprising a first ring of gear teeth and the rotating portion comprising a second ring of gear teeth, the first ring of gear teeth engaging with the second ring of gear teeth when the rotating portion is rotated in the first direction and the first ring of gear teeth disengaging with the second ring of gear teeth when the rotating portion is rotated in the second direction.

5. An endovascular introducer as in claim 4 wherein the one way clutch assembly further comprises a resilient apparatus resiliently engaging the first ring of gear teeth engaging with the second ring of gear teeth.

6. An endovascular introducer as in claim 4 wherein the first ring of gear teeth and the second ring of gear teeth each comprise a plurality of teeth, each tooth comprising leading flat face and an angled trailing face when viewed in the first direction whereby when the rotating portion is rotated in the first direction the leading flat face of a tooth of the rotating portion engages with the leading flat face of a tooth of the rotation transfer sleeve to transfer rotation and when the rotating portion is rotated in the second direction the angled trailing face of a tooth of the rotating portion engages with the angled trailing face of a tooth of the rotation transfer sleeve and the angled faces of the respective teeth cause separation of the respective gear rings thereby preventing transfer of rotation.

7. An endovascular introducer as in claim 1 wherein the fixed portion comprises first and second trigger wire release mechanisms at a distal end thereof, the first and second trigger wire release mechanisms being connected to trigger wires which engage the sent graft to temporarily retain the stent graft to the stent graft deployment device, the first and second trigger wire release mechanisms being movable to be disengaged from the distal end of the fixed portion to pull the trigger wires to release the stent graft from the stent graft deployment device.

8. An endovascular introducer as in claim 7 wherein the first and second trigger wire release mechanisms are engaged onto the distal end of the fixed portion by respective interengaging screw threads and the first and second trigger wire release mechanisms are movable to be disengaged from the distal end of the fixed portion by being rotated with respect to the fixed portion.

9. An endovascular introducer as in claim 8 wherein each of the first and second trigger wire release mechanisms comprise a rotating portion and a linearly moving portion, the linearly moving portion being engaged into a longitudinal track in the fixed portion and the interengaging screw thread being on the rotating portion and the trigger wires being affixed to the linearly moving portion.

10. An endovascular introducer as in claim 1 wherein the sheath comprises a sheath hub and the sheath hub is releasably engaged with a proximal end of the second part.

11. An endovascular introducer as in claim 10 wherein the releasable engagement of the sheath hub with the proximal end of the second part comprises a hub shroud around the hub and a locking ring, the locking ring engaging the hub shroud and incorporating a bayonet interconnection with the proximal end of the second part, whereby rotation of the locking ring disengages the bayonet interconnection with the proximal end of the second part such that the hub shroud and locking ring can be removed from the proximal end of the second part.

12. An endovascular introducer comprising in combination, a handle assembly, a stent graft deployment device and a stent graft retained on the stent graft deployment device, the handle assembly including a first part and a second part, the second part to be moved relative to the first part, the first part comprising a fixed portion to be gripped and held by a user, a rotating portion to be rotated with the fixed portion and a rotation transfer sleeve, the rotation transfer sleeve being within the rotating portion and connected to the rotating portion by a one way clutch arrangement whereby rotation of the rotating portion in a first direction transfers rotation to the rotation transfer sleeve and rotation of the rotating portion in a direction opposite to the first direction does not transfer rotation to the rotation transfer sleeve;

the rotation transfer sleeve and the second part comprising co-acting first screw threads whereby rotation of the rotating portion of the first part with respect to the second part in the first direction transferred through the one way clutch arrangement causes relative longitudinal motion between the first part and the second part, the one way clutch assembly comprises the rotation transfer sleeve comprising a first ring of gear teeth and the rotating portion comprising a second ring of gear teeth, the first ring of gear teeth engaging with the second ring of gear teeth when the rotating portion is rotated in the first direction and the first ring of gear teeth disengaging with the second ring of gear teeth when the rotating portion is rotated in the second direction and a spring to engage the first ring of gear teeth with the second ring of gear teeth; the deployment device including a pusher assembly, the stent graft being mounted onto the pusher assembly and a sheath to cover the stent graft on the pusher assembly and to retain the stent graft in a compressed condition on the pusher assembly, the sheath being relatively movable with respect to the pusher assembly, the pusher assembly being connected to the first part and the sheath being connected to the second part whereby retraction of the second part with respect to the first part by the relative rotation thereof causes the sheath to be retracted at least partially from the stent graft on the pusher assembly.

* * * * *